(12) United States Patent
Kim (10) Patent No.: US 9,211,076 B2
(45) Date of Patent: Dec. 15, 2015

(54) METHOD AND DEVICE TO MEASURE BIOSIGNAL

(71) Applicant: SAMSUNG ELECTRONICS CO., LTD., Suwon-si (KR)

(72) Inventor: Youn Ho Kim, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 14/306,411

(22) Filed: Jun. 17, 2014

(65) Prior Publication Data

US 2014/0371611 A1  Dec. 18, 2014

(30) Foreign Application Priority Data

Jun. 17, 2013  (KR) .................. 10-2013-0068864

(51) Int. Cl.
*A61B 5/04* (2006.01)
*A61B 5/0424* (2006.01)
*A61B 5/0416* (2006.01)

(52) U.S. Cl.
CPC ............ *A61B 5/0424* (2013.01); *A61B 5/0416* (2013.01); *A61B 2560/0209* (2013.01); *A61B 2562/0214* (2013.01); *A61B 2562/226* (2013.01); *A61B 2562/227* (2013.01)

(58) Field of Classification Search
CPC ............... A61B 2560/0209; A61B 2562/0214; A61B 2562/226; A61B 2562/227; A61B 5/0416; A61B 5/0424
See application file for complete search history.

(56) References Cited

U.S. PATENT DOCUMENTS

| 2007/0208233 | A1 | 9/2007 | Kovacs |
| 2011/0043225 | A1 | 2/2011 | Sullivan et al. |
| 2012/0088999 | A1 | 4/2012 | Bishay et al. |
| 2012/0265080 | A1 | 10/2012 | Yu et al. |
| 2014/0088394 | A1* | 3/2014 | Sunderland ............ 600/373 |

FOREIGN PATENT DOCUMENTS

| EP | 1 275 342 A2 | 1/2003 |
| JP | 7-323023 A | 12/1995 |
| JP | 2003-275185 A | 9/2003 |
| KR | 10-2005-0121472 A | 12/2005 |
| KR | 10-2006-0050892 A | 5/2006 |

(Continued)

OTHER PUBLICATIONS

International Search Report issued Apr. 22, 2014 in corresponding International Patent Application No. PCT/KR2014/000446 (3 pages, in English).

*Primary Examiner* — George Manuel
(74) *Attorney, Agent, or Firm* — NSIP Law (57) ABSTRACT

Provided is a biosignal measurement method and device that may measure a biosignal by connecting a simple electrode or a capacitive coupling active electrode to a biosignal processor to analyze the biosignal. The biosignal processor may change a frequency band in which the biosignal is to be filtered based on a type of the connected electrode. The biosignal measurement device includes a first signal connector capable of removably attaching to an electrode unit that is configured to sense a biosignal, wherein the first signal connector is configured to receive the biosignal from the electrode unit; a power supplier configured to supply power to the electrode unit in response to the power supplier being connected to the electrode unit; and a signal processor configured to process the biosignal received by the first signal connector.

20 Claims, 7 Drawing Sheets

(56) References Cited

FOREIGN PATENT DOCUMENTS

| KR | 10-2006-0079233 A | 7/2006 |
| KR | 10-2009-0131542 A | 12/2009 |
| KR | 10-2011-0004660 A | 1/2011 |
| WO | WO 2012/075497 A1 | 6/2012 |

\* cited by examiner

FIG. 6D

METHOD AND DEVICE TO MEASURE BIOSIGNAL

CROSS-REFERENCE TO RELATED APPLICATIONS

This application claims the benefit under 35 U.S.C. §119(a) of Korean Patent Application No. 10-2013-0068864, filed on Jun. 17, 2013, in the Korean Intellectual Property Office, the entire disclosure of which is incorporated herein by reference for all purposes.

BACKGROUND

1. Field

The following description relates to a method and device to measure a biosignal.

2. Description of Related Art

Ubiquitous health (U-health) may refer to a service that provides health care and medical treatment, such as diagnosis, treatment, and protection. For example, by connecting a patient to a doctor without restrictions on time and place using information technology (IT) network, such as, for example, the Internet, a mobile phone, and a bi-directional cable television (TV). U-health may also refer to a technique of monitoring a biosignal of a patient without restrictions on time and place to provide such service. For example, a general electrocardiogram (ECG) measurement device to measure an ECG uses conductive gel and is generally used in a hospital environment. An ECG may be measured without using conductive gel where a user wears clothes and is partaking in the activities of everyday life. For example, a technique of measuring a biosignal in a noncontact manner may be utilized.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided a biosignal measurement device including a first signal connector capable of removably attaching to an electrode unit that is configured to sense a biosignal, wherein the first signal connector is configured to receive the biosignal from the electrode unit; a power supplier configured to supply power to the electrode unit in response to the power supplier being connected to the electrode unit; and a signal processor configured to process the biosignal received by the first signal connector.

The signal processor may be further configured to maintain a signal processing frequency band of a filter when the power supplier is disconnected from the electrode unit; and to change the signal processing frequency band of the filter when the power supplier is connected to the electrode unit.

The signal processor may be further configured to operate in a first frequency band when the power is not supplied from the power supplier; and to operate in a second frequency band when the power is not supplied from the power supplier.

The first frequency band may be wider than the second frequency band.

The biosignal measurement device may include a fixing unit configured to fix the biosignal measurement device to at least one of a body or clothes.

The electrode unit, may include at least one electrode configured to sense the biosignal; and a second signal connector capable of removably attaching to the first signal connector, wherein the second signal connector is configured to transfer the biosignal to the first signal connector.

The electrode unit may include at least one capacitive coupling active electrode configured to sense the biosignal; a second signal connector capable of removably attaching to the first signal connector, wherein the second signal connector is configured to transfer the biosignal to the first signal connector; and a second power connector configured to provide power supplied from the power supplier to the to the at least one capacitive coupling active electrode.

The biosignal measurement device may include a first power connector configured to supply power to the electrode unit form the power supplier.

The biosignal measurement device may include a communicator configured to transmit the processed biosignal to an external device.

In another general aspect, there is provided a biosignal measurement device including an electrode unit configured to sense a biosignal; a first signal connector capable of removabely attaching to the electrode unit, wherein the first signal connector is configured to receive the biosignal from the electrode unit; a power connector configured to receive power from the electrode unit in response to the power connector being connected to the electrode unit; and a signal processor configured to process the biosignal received by the first signal connector.

The signal processor may be further configured to maintain a signal processing frequency band of a filter when the power connector is disconnected from the electrode unit, and to change the signal processing frequency band of the filter when the power connector is connected to the electrode unit.

The signal processor may be further configured to operate in a first frequency band when the power is not supplied from the power connector; and to operate in a second frequency band when the power is received by the power connector.

The signal processor may be configured to operate in a frequency band for a capacitive coupling active electrode when the power is received by the power connector.

The biosignal measurement device may include a fixing unit configured to fix the biosignal measurement device to at least one of a body or clothes.

The electrode unit may include at least one electrode configured to sense the biosignal; and a second signal connector capable of removably attaching to the first signal connector, wherein the second signal connector is configured to transfer the biosignal to the first signal connector.

The electrode unit may include at least one capacitive coupling active electrode configured to sense the biosignal; a second signal connector capable of removably attaching to the first signal connector, wherein the second signal connector is configured to transfer the biosignal to the first signal connector; and a power supplier configured to supply power to the capacitive coupling active electrode and the power connector.

In another general aspect, there is provided a method to measure a biosignal, the method including determining a connection between an electrode unit and a power connector; supplying power to the electrode unit in response to the detected connection; sensing a biosignal at the electrode unit; and processing the sensed biosignal at a biosignal processor.

The processing may include maintaining a signal processing frequency band of a filter in response to the power not being supplied to the electrode unit; and changing the signal processing frequency band of the filter in response to the power being supplied to the electrode unit.

The processing may include processing the biosignal in a first frequency band in response to the connection not being detected; and processing the biosignal in a second frequency band in response to the connection being detected.

The processing may include operating a filter in a frequency band for a capacitive coupling active electrode in response to the connection being detected.

The sensing of the biosignal may include sensing the biosignal through at least one electrode, and the processing may include processing the biosignal in a first frequency band in response to the connection not being detected.

The supplying power may include supplying power to at least one capacitive coupling active electrode; the sensing of the biosignal may include sensing the biosignal through the capacitive coupling active electrode; and the processing may include processing the biosignal in a second frequency band in response to the connection being detected.

The processing may include processing the biosignal in a frequency band between 0.1 Hz to 150 Hz in response to the connection not being detected; and processing the biosignal in the frequency band between 5 Hz to 35 Hz in response to the connection being detected.

Other features and aspects will be apparent from the following detailed description, the drawings, and the claims.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Figure 1:
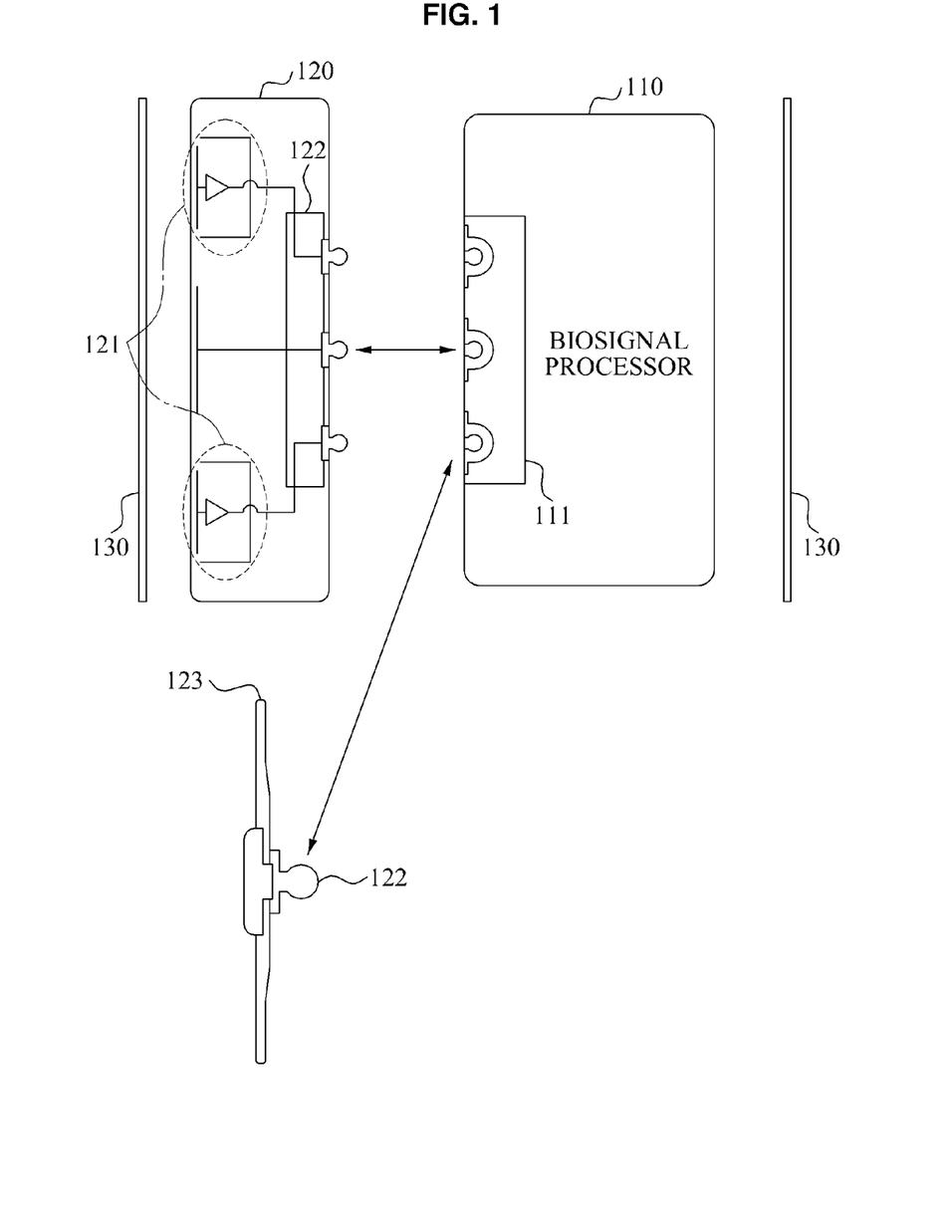
FIG. 1 is a diagram illustrating an example of a biosignal measurement device.

FIG. 1 illustrates an example of a biosignal measurement device. Referring to FIG. 1, the biosignal measurement device includes a biosignal processor 110, an electrode unit 120, and a fixing unit 130. Biosignal may include all signals that can be measured and monitored from biological beings, such as, for example, electrocardiogram (ECG) signal, electrooculogram (EOG) signal, electromyogram (EMG) signal, electroencephalogram (EEG) signal, Mechanomyogram (MMG) signal, Galvanic skin response (GSR) signal, and Magnetoencephalogram (MEG).

The electrode unit 120 may include an electrode capable of sensing a biosignal. For example, the electrode unit 120 may include an active electrode, such as, for example, a capacitive coupling active electrode 121 and a simple metal electrode 123. The electrode unit 120 is connected to the biosignal processor 110 through a signal connector 122 provided in a physically connectable structure. The electrode unit 120 including different types of electrodes, for example, the metal electrode 123 and the capacitive coupling active electrode 121, may be selectively connected to at least one signal processor 110 through the signal connector 122 provided in a similar form, based on a predetermined condition.

For example, when a biosignal of a human body is required to be measured, the biosignal may be measured by connecting the biosignal processor 110 with the metal electrode 123 in a state in which the body is restrained. As another example, when a biosignal is required to be measured without restraining a body, for example, when a user is in a sleeping state, the biosignal may be measured by connecting the biosignal processor 110 with the capacitive coupling active electrode 121 that does not require restraining the body.

The biosignal processor 110 may extract a waveform of the measured biosignal by processing the measured biosignal. The biosignal processor 110 may be connected to the electrode unit 120 through a signal connector 111. The biosignal processor 110 may differently process a biosignal based on whether power is supplied to the electrode unit 120, which will be further described with reference to FIG. 2 through FIG. 5.

The fixing unit 130 may fix the biosignal measurement device to a body or to the clothes worn by a person. Referring to FIG. 1, the fixing unit 130 is mounted to at least one of the electrode unit 120 and the biosignal processor 110 of the biosignal measurement device. Example of the fixing unit 130 fixing the biosignal measurement device to the body will be further described with reference to FIG. 6.

According to a non-exhaustive example, a user may measure a biosignal by selectively applying a direct contact using a simple electrode based on a change in environment or an indirect contact using a capacitive coupling active electrode. Accordingly, a user may measure biosignal more conveniently. For example, when the user is participating in active exercise or when the ECG morphology of the user needs to be accurately observed, a simple electrode having an adhesive property may be attached to the biosignal measurement device around the heart of a user. As another example, when a motion of the user is limited, such as when the user is sleeping, and when a binding force of a contact needs to be reduced for measuring biosignal, the capacitive coupling active electrode 121 may be attached to the user and may be used to measure a biosignal.

Figure 2:
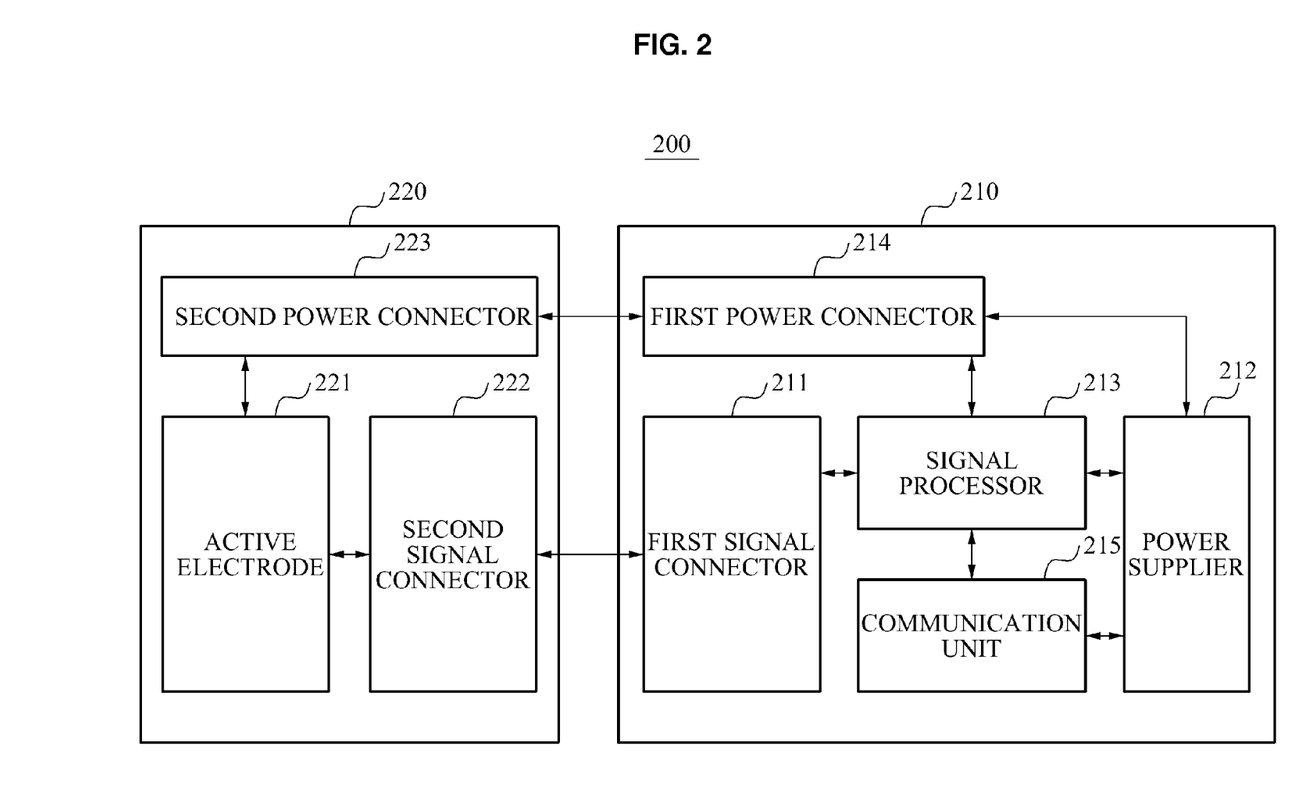
FIG. 2 is a diagram illustrating an example of a biosignal measurement device.

FIG. 2 illustrates an example of a biosignal measurement device 200. Referring to FIG. 2, the biosignal measurement device 200 includes a biosignal processor 210 and an electrode unit 220. The biosignal processor 210 may include a first signal connector 211 and a first power connector 214. The electrode unit 220 may include a second signal connector 222 and a second power connector 223.

The biosignal connector 210 includes the first signal connector 211, a power supplier 212, a signal processor 213, the first power connector 214, and a communication unit 215.

The first signal connector 211 has a structure that is capable of being physically connectable to the electrode unit 220, which is configured to sense a biosignal. The first signal connector 211 is connected to the electrode unit 220 through the second signal connector 222 to receive the biosignal. Similarly, the electrode unit 220 has a structure that is capable of being physically connectable to the first signal connector 211. The first signal connector 211 and the electrode unit 220 are physically connectable and may be connected to each other or may be separate from each other depending on the requirement. For example, a magnet may be used for the connectable structure. The first signal connector 211 may transfer at least one signal through each separate path and may also receive at least one signal through each separate path.

When the first power connector 214 is connected to the second power connector 223, the power supplier 212 may supply power to the electrode unit 220. The power supplier 212 may also supply power to operate the signal processor 213 and the communication unit 215.

The signal processor 213 may process a biosignal provided from the first signal connector 211. The signal processor 213 may include, for example, an analog front end (AFE) and a filter. The signal processor 213 may modify a scheme of processing a biosignal based on a type of an electrode included in the electrode unit 220 connected to the biosignal processor 210.

When the power is not supplied from the power supplier 212, the signal processor 213 may operate in a first frequency band. When the power is supplied from the power supplier 212, the signal processor 213 may operate in a second frequency band. For example, when the power supplier 212 is disconnected from the electrode unit 220, the signal processor 213 may maintain a signal processing frequency band of the filter. When the power supplier 212 is connected to the electrode unit 220, the signal processor 213 may change the signal processing frequency band of the filter. In this example, the second frequency band may have a width less than the first frequency band. For example, the second frequency band may include a frequency band for a capacitive coupling active electrode.

The signal processor 213 may include a right-leg-driven (RLD) circuit or other methods to reduce common-mode interference. To cancel common-mode noise, the signal processor 213 may receive two biosignals from the electrode unit 220 through the second signal connector 222 and may feed back a single signal including common-mode noise to a body through the electrode unit 220.

The first power connector 214 may be connected to the second power connector 223 to provide power to the electrode unit 220. For example, when the electrode unit 220 includes a capacitive coupling active electrode, the power may be provided to an operational amplifier used for the capacitive coupling active electrode.

The first power connector 214 may detect whether to provide the power to the electrode unit 220. For example, the first power connector 214 may include a switch function. When the switch is turned on, the first power connector 214 may detect that the power is to be provided to the electrode unit 220. When the switch is turned off, the first power connector 214 may detect that the power is not to be provided to the electrode unit 220. When the first power connector 214 is connected to the second power connector 223, the switch may be turned on.

The communication unit 215 may transmit a result of processing the biosignal at the signal processor 213 to an external device. The external device may refer to any device capable of performing a communication function in order to receive the result from the biosignal measurement device 200. As a non-exhaustive illustration only, an external device described herein may refer to devices such as, for example, a cellular phone, a smart phone, a wearable smart device (such as, for example, a ring, a watch, a pair of glasses, a bracelet, an ankle bracket, a belt, a necklace, an earring, a headband, a helmet, a device embedded in the cloths or the like), a personal computer (PC), a tablet personal computer (tablet), a phablet, a personal digital assistant (PDA), a digital camera, a portable game console, an MP3 player, a portable/personal multimedia player (PMP), a handheld e-book, an ultra mobile personal computer (UMPC), a portable lab-top PC, a global positioning system (GPS) navigation, and devices such as a high definition television (HDTV), an optical disc player, a DVD player, a Blue-ray player, a setup box, or any other device capable of wireless communication or network communication consistent with that disclosed herein. In a non-exhaustive example, the external device may be self-mountable on the body of the user, such as, for example, the glasses or the bracelet. In another non-exhaustive example, the external device may be mounted on the body of the user through an attaching device, such as, for example, attaching a smart phone or a tablet to the arm of a user using an armband, or hanging the external device around the neck of a user using a lanyard.

The electrode unit 220 may include an active electrode 221, the second signal connector 222, and the second power connector 223. For example, the electrode unit 220 including the active electrode 221 may be used to measure a biosignal through a direct contact without restraining the body. For example, the active electrode 221 may be applied to a body of a user when the user is sleeping, undertaking an exercise, such as a power walking or jogging. The active electrode 221 may also be applied to a body of a user to detect drowsiness, and to monitor the daily stress level.

The active electrode 221 may sense a biosignal through capacitive coupling with a body. For example, the active electrode 221 may include, as a capacitive coupling active electrode, a shield configured to prevent external noise, an electrode face configured to establish a contact with the body to sense a biosignal, and an operational amplifier that is supplied with power and that operates to amplify the biosignal.

The second signal connector 222 has a structure that is capable of being physically connected to the first signal connector 211. The second signal connector 222 is connected to the first signal connector 211 to transfer the sensed biosignal to the biosignal processor 210. In this example, when the signal processor 213 includes an RLD circuit, the second signal processor 222 may feed back, to the body, a signal transferred from the first signal connector 221. The signal transferred from the first signal connector 221 may include common-mode noise.

The second power connector 223 may provide, to the capacitive coupling active electrode, the power supplied from the first power connector 214.

The electrode unit 220 may include a metal electrode and the second signal connector 222 without including the second power connector 223. In this example, the electrode unit 220 may transfer a biosignal to the biosignal processor 210 without being supplied with the power, which differs from a case in which the electrode unit 220 includes the active electrode 221. For example, the electrode unit 220 including the simple electrode may be used to measure a biosignal by restraining the body or through a direct contact. The simple electrode may include a wet electrode, and may be applied when a more exact test is required because the user, for example, suffers from the heart disease and does strenuous exercise.

Figure 3:
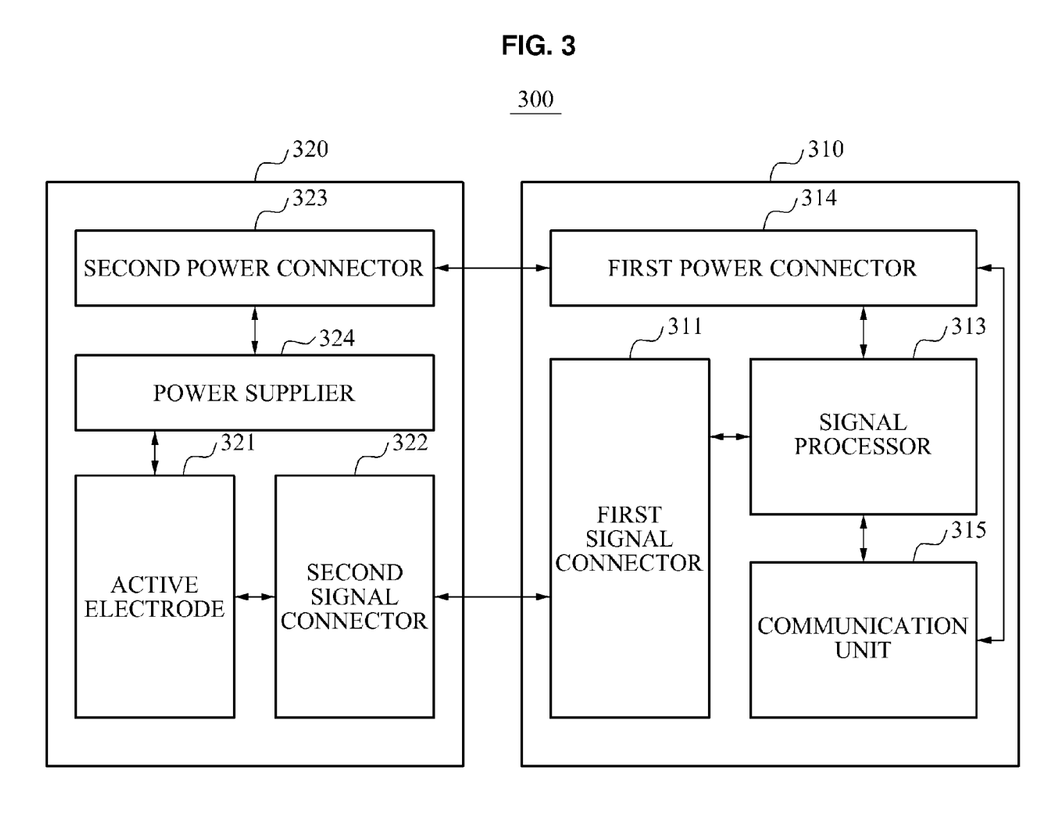
FIG. 3 is a diagram illustrating another example of a biosignal measurement device.

FIG. 3 illustrates another example of a biosignal measurement device 300. Referring to FIG. 3, a power supplier 324 is mounted to an electrode unit 320 instead of being mounted to a biosignal processor 310, which differs from the example of FIG. 2.

The biosignal processor 310 includes a first signal connector 311, a signal processor 313, a first power connector 314, and a communication unit 315. The first signal connector 311, the signal processor 313, and the communication unit 315 may be similar to the first signal connector 211, the signal processor 213, and the communication unit 215, respectively, of FIG. 2. When the first power connector 314 is connected to the electrode unit 320, the first power connector 314 may be supplied with the power from the electrode unit 320. The first power connector 314 may transfer the power to operate the signal processor 313 and the communication unit 315.

The electrode unit 320 includes an active electrode 321, a second signal connector 322, a second power connector 323, and the power supplier 324. The active electrode 321 and the second signal connector 322 may be similar to the active electrode 221 and the second signal connector 222, respectively, of FIG. 2. The second power connector 323 may provide the power supplied from the power supplier 324 to the first power connector 314 and to the active electrode 321. The power supplier 324 may supply power so as to operate the active electrode 321. When the first power connector 314 is connected to the second power connector 323, the power supplier 324 may transfer the power to the biosignal processor 310.

Figure 4:
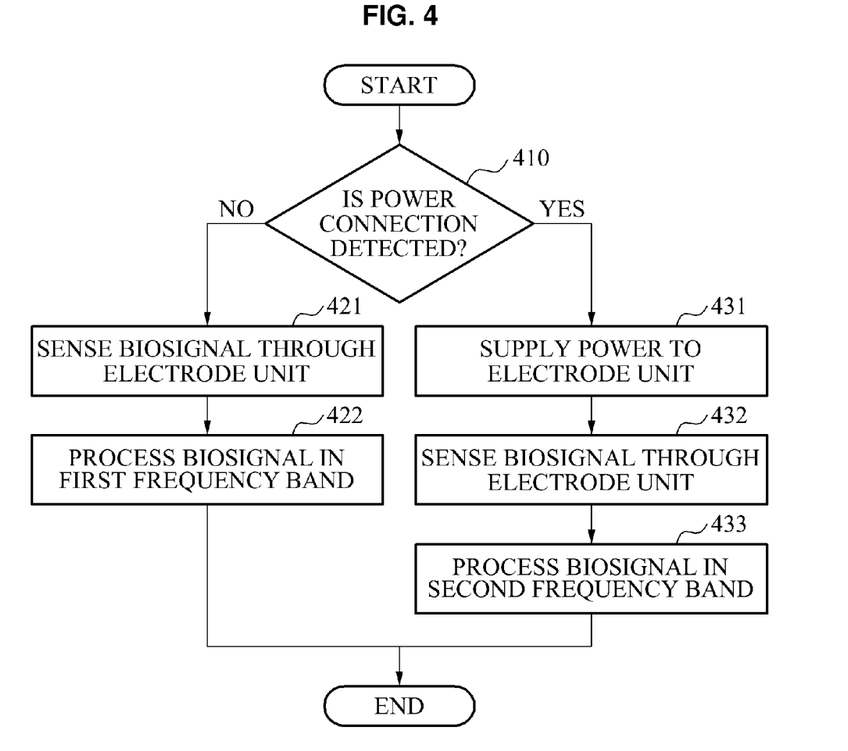
FIG. 4 is a diagram illustrating an example of a method to measure a biosignal.

FIG. 4 illustrates an example of a method to measure a biosignal. The operations in FIG. 4 may be performed in the sequence and manner as shown, although the order of some operations may be changed or some of the operations omitted without departing from the spirit and scope of the illustrative examples described. Many of the operations shown in FIG. 4 may be performed in parallel or concurrently. The description of FIGS. 1-3 is also applicable to FIG. 4, and thus will not be repeated here.

In 410, a connection between an electrode unit and a power connector is detected. For example, a determination may be made whether a first power connector and a second power connector are connected. The connection may be detected when switches included in the first power connector and the second power connector are turned on. A signal processor may process a biosignal sensed by the electrode unit as follows.

When the power connection is not detected, in 421, the electrode unit senses a biosignal through at least one electrode. For example, the electrode unit may include a simple electrode.

When the connection is not detected, in 422, the biosignal is processed in a first frequency band. The first frequency band may include a band suitable for processing the biosignal using a direct contact type electrode, for example, a metal electrode. For example, a biosignal corresponding to the first frequency band may pass through a band pass filter (BPF).

When a frequency band of the signal processor is set by default to the first frequency band, a signal processing frequency band of a filter included in the signal processor may be maintained when power is not being supplied. When the frequency band set by default is a second frequency band, the signal processing frequency band of the filter may be changed to the first frequency band when power is not being supplied.

Conversely, when the power connection is detected, in 431, power is supplied to the electrode unit. The power supplier may supply the power to at least one capacitive coupling active electrode.

In 432, the biosignal is sensed through the electrode unit. The electrode unit may sense the biosignal using the capacitive coupling active electrode.

When the connection is detected, in 433, the biosignal is processed in the second frequency band. The second frequency band may include a frequency band for a capacitive coupling active electrode. For example, a biosignal corresponding to the second frequency band may pass through a BPF.

When a frequency band of the signal processor is set by default to the first frequency band, the signal processing frequency band of the filter included in the signal processor may be changed to the second frequency band while the power is being supplied. When the frequency band of the signal processor is set by default to the second frequency band, the signal processing frequency band of the filter may be maintained while the power is being supplied.

Figure 5:
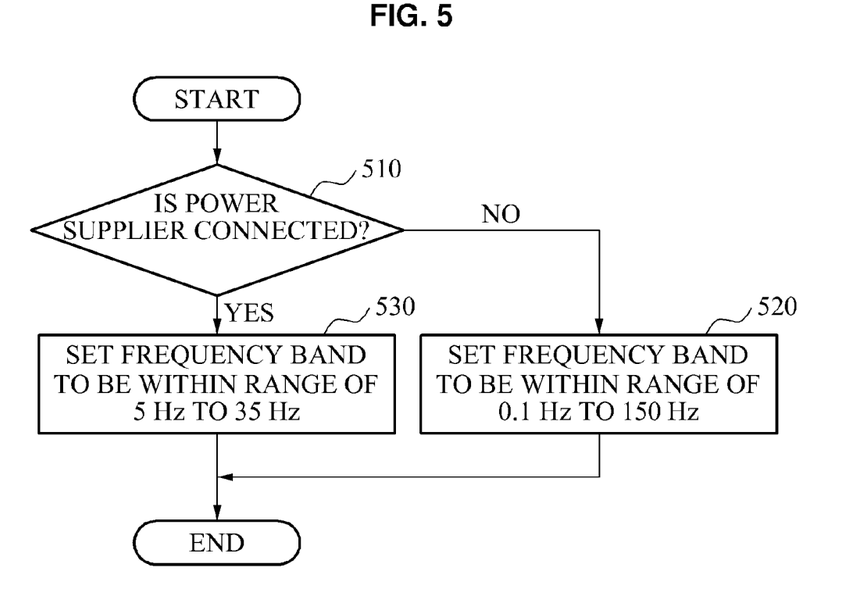
FIG. 5 is a diagram illustrating another example of a method to measure a biosignal.

FIG. 5 illustrates another example of a method to measure a biosignal. In this example, the biosignal may be an ECG signal. The operations in FIG. 5 may be performed in the sequence and manner as shown, although the order of some operations may be changed or some of the operations omitted without departing from the spirit and scope of the illustrative examples described. Many of the operations shown in FIG. 5 may be performed in parallel or concurrently. The description of FIGS. 1-4 is also applicable to FIG. 5, and thus will not be repeated here.

In 510, it is determined whether a power supplier is connected. For example, whether power is supplied from a biosignal processor to an electrode unit, or whether the power is supplied from the electrode unit to the biosignal processor may be detected through the connection to the power supplier.

When the connection with a power supply is not detected, a signal processing frequency band of a filter is set to be within a range of 0.1 Hz to 150 Hz in 520. For example, when a switch of the power supplier is turned off, the signal processing frequency band of the filter may be set to be a first frequency band, for example, within the range of 0.1 Hz to 150 Hz in order to observe the overall waveform of ECG using a simple electrode.

When the connection with a power supply is detected, the signal processing frequency band of the filter is set to be within a range of 5 Hz to 35 Hz. For example, when the switch of the power supplier is turned on, the signal processing frequency band of the filter may be set to a second frequency band, for example, within the range of 5 Hz to 35 Hz in order to observe R-peaks of ECG using a capacitive coupling active electrode. The capacitive coupling active electrode is robust against motion artifacts and measures a relatively simple waveform, for example, R-peaks of ECG compared to the simple electrode. Accordingly, the signal processor may process a biosignal using a relatively narrow band.

According to non-exhaustive examples, a direct contact scheme using a simple electrode and an indirect contact scheme using an indirect electrode may be selectively used in order to measure a biosignal. For example, when a user moves a lot in everyday life, the simple electrode may be used. In another example, to prevent an electrode from obstructing a sleeping user, the capacitive coupling active electrode may be used.

Figure 6A:
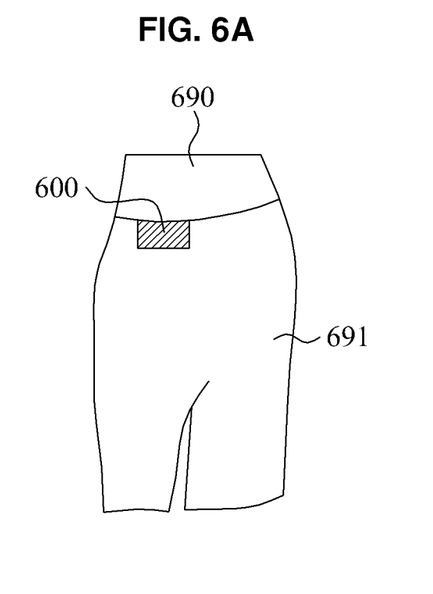
FIGS. 6A through 6D are diagrams illustrating examples of a fixing unit of a biosignal measurement device.

FIGS. 6A through 6D illustrate examples of a fixing unit 630 of a biosignal measurement device 600. The fixing unit 630 may be similar to the fixing unit 130 of FIG. 1. FIG. 6A illustrates an example in which the biosignal measurement device 600 is attached to a material 691, for example, undergarment by the fixing unit 630 to contact to the skin of a user 690. The fixing unit 630 is mounted to an electrode unit or a biosignal processor of the biosignal measurement device 600 to fix the biosignal measurement device 600 to another object. For example, the other object may include the skin of the user 690 and clothes of the user 690, for example, outer garments and undergarments.

Figure 6B:
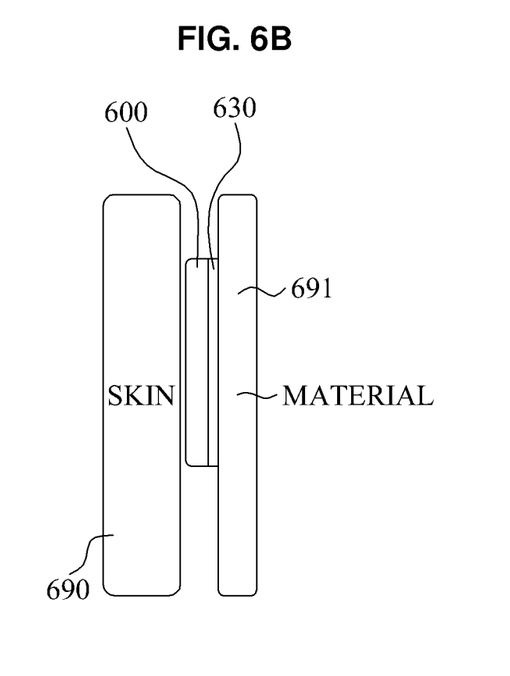
Figure 6C:
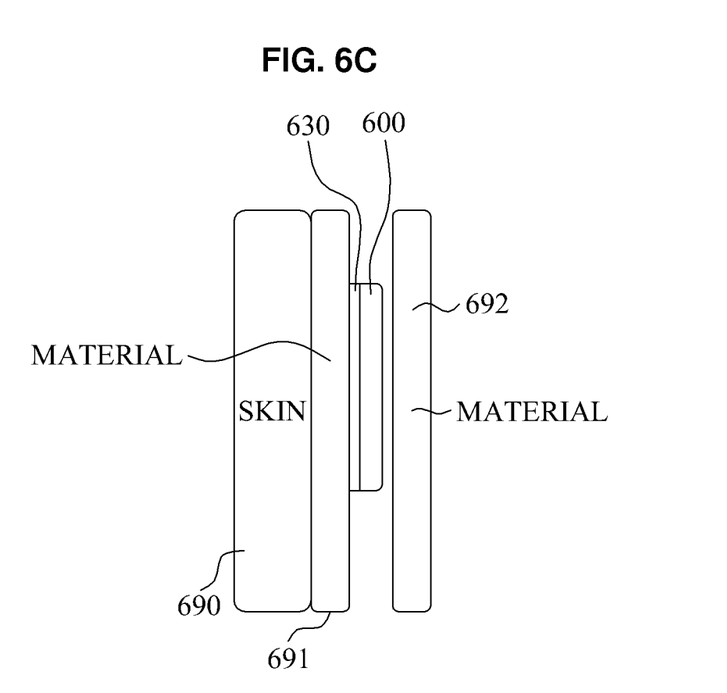
Figure 6D:
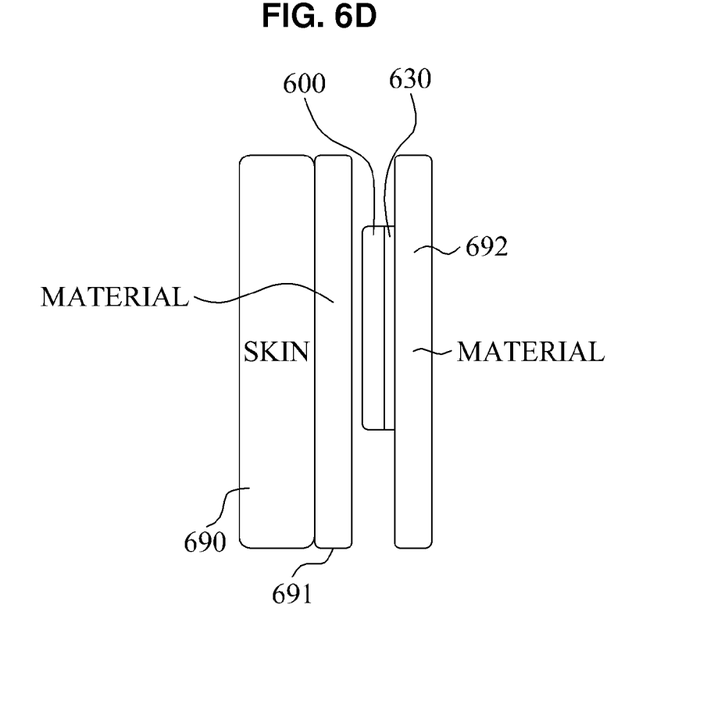

Referring to FIG. 6B, the biosignal measurement 600 is fixed and directly contacts with the skin of user 690 by attaching the fixing unit 630 to an inside of the material 691, for example, undergarment. Referring to FIG. 6C, the biosignal measurement device 600 indirectly contacts with the skin of user 690 by attaching the fixing unit 630 to an outside of the material 691 and measures a biosignal using a capacitive coupling active electrode scheme. Referring to FIG. 6D, the biosignal measurement device 600 measures a biosignal using a capacitive coupling active electrode scheme after fixing the biosignal measurement device 600 to an inside of another material 692, for example, an outer garment using the fixing unit 630.

The processes, functions, and methods described above including a method for beamforming can be written as a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device that is capable of providing instructions or data to or being interpreted by the processing device. The software also may be distributed over network coupled computer systems so that the software is stored and executed in a distributed fashion. In particular, the software and data may be stored by one or more non-transitory computer readable recording mediums. The non-transitory computer readable recording medium may include any data storage device that can store data that can be thereafter read by a computer system or processing device. Examples of the non-transitory computer readable recording medium include read-only memory (ROM), random-access memory (RAM), Compact Disc Read-only Memory (CD-ROMs), magnetic tapes, USBs, floppy disks, hard disks, optical recording media (e.g., CD-ROMs, or DVDs), and PC interfaces (e.g., PCI, PCI-express, WiFi, etc.). In addition, functional programs, codes, and code segments for accomplishing the example disclosed herein can be construed by programmers skilled in the art based on the flow diagrams and block diagrams of the figures and their corresponding descriptions as provided herein.

The apparatuses and units described herein may be implemented using hardware components. The hardware components may include, for example, controllers, sensors, processors, generators, drivers, and other equivalent electronic components. The hardware components may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The hardware components may run an operating system (OS) and one or more software applications that run on the OS. The hardware components also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a hardware component may include multiple processors or a processor and a controller. In addition, different processing configurations are possible, such a parallel processors.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A biosignal measurement device, comprising:
   a first signal connector capable of removably attaching to an electrode unit that is configured to sense a biosignal, wherein the first signal connector is configured to receive the biosignal from the electrode unit;
   a power supplier configured to supply power to the electrode unit, in response to the power supplier being connected to the electrode unit; and
   a signal processor configured to process the biosignal received by the first signal connector, to maintain a signal processing frequency band of a filter when the power supplier is disconnected from the electrode unit, and to change the signal processing frequency band of the filter when the power supplier is connected to the electrode unit.

2. The biosignal measurement device of claim 1, wherein the signal processor is further configured:
   to operate in a first frequency band when the power is not supplied from the power supplier; and
   to operate in a second frequency band when the power is supplied from the power supplier.

3. The biosignal measurement device of claim 2, wherein the first frequency band is wider than the second frequency band.

4. The biosignal measurement device of claim 1, further comprising:
   a fixing unit configured to fix the biosignal measurement device to at least one of a body or clothes.

5. The biosignal measurement device of claim 1, wherein the electrode unit comprises:
   at least one electrode configured to sense the biosignal; and
   a second signal connector capable of being removably attached to the first signal connector, wherein the second signal connector is configured to transfer the biosignal to the first signal connector.

6. The biosignal measurement device of claim 1, wherein the electrode unit comprises:
   at least one capacitive coupling active electrode configured to sense the biosignal;
   a second signal connector capable of being removably attached to the first signal connector, wherein the second signal connector is configured to transfer the biosignal to the first signal connector; and
   a second power connector configured to provide power supplied from the power supplier at least one capacitive coupling active electrode.

7. The biosignal measurement device of claim 1, further comprising a first power connector configured to supply power to the electrode unit form the power supplier.

8. The biosignal measurement device of claim 1, further comprising a communicator configured to transmit the processed biosignal to an external device.

9. A biosignal measurement device, comprising:
   an electrode unit configured to sense a biosignal;
   a first signal connector capable of removabely attaching to the electrode unit, wherein the first signal connector is configured to receive the biosignal from the electrode unit;
   a power connector configured to receive power from the electrode unit, in response to the power connector being connected to the electrode unit; and
   a signal processor configured to process the biosignal received by the first signal connector, to operate in a first frequency band when the power is not supplied from the power connector, and to operate in a second frequency band when the power is received by the power connector.

10. The biosignal measurement device of claim 9, wherein the signal processor is further configured:
    to maintain a signal processing frequency band of a filter when the power connector is disconnected from the electrode unit, and
    to change the signal processing frequency band of the filter when the power connector is connected to the electrode unit.

11. The biosignal measurement device of claim 9, wherein the signal processor is configured to operate in a frequency band for a capacitive coupling active electrode when the power is received by the power connector.

12. The biosignal measurement device of claim 9, further comprising:
    a fixing unit configured to fix the biosignal measurement device to at least one of a body or clothes.

13. The biosignal measurement device of claim 9, wherein the electrode unit comprises:
    at least one electrode configured to sense the biosignal; and
    a second signal connector capable of being removably attached to the first signal connector, wherein the second signal connector is configured to transfer the biosignal to the first signal connector.

14. The biosignal measurement device of claim 9, wherein the electrode unit comprises:
    at least one capacitive coupling active electrode configured to sense the biosignal;
    a second signal connector capable of being removably attached to the first signal connector, wherein the second signal connector is configured to transfer the biosignal to the first signal connector; and
    a power supplier configured to supply power to the capacitive coupling active electrode and the power connector.

15. A method to measure a biosignal, the method comprising:
    determining a connection between an electrode unit and a power connector;
    supplying power to the electrode unit, in response to the detected connection;
    sensing a biosignal at the electrode unit through at least one electrode; and
    processing the sensed biosignal at a biosignal processor,
    wherein the processing comprises processing the biosignal in a first frequency band, in response to the connection not being detected.

16. The method of claim 15, wherein the processing comprises:
    maintaining a signal processing frequency band of a filter, in response to the power not being supplied to the electrode unit; and
    changing the signal processing frequency band of the filter, in response to the power being supplied to the electrode unit.

17. The method of claim 15, wherein the processing comprises
    processing the biosignal in a second frequency band, in response to the connection being detected.

18. The method of claim 15, wherein the processing comprises operating a filter in a frequency band for a capacitive coupling active electrode, in response to the connection being detected.

19. The method of claim 15, wherein:
    the supplying power comprises supplying power to at least one capacitive coupling active electrode;
    the sensing of the biosignal comprises sensing the biosignal through the capacitive coupling active electrode; and
    the processing comprises processing the biosignal in a second frequency band, in response to the connection being detected.

20. The method of claim 15, wherein the processing comprises:
    processing the biosignal in a frequency band between 0.1 Hz to 150 Hz, in response to the connection not being detected; and
    processing the biosignal in the frequency band between 5 Hz to 35 Hz, in response to the connection being detected.

* * * * *